(12) United States Patent
Vess

(10) Patent No.: US 8,535,253 B2
(45) Date of Patent: Sep. 17, 2013

(54) TUBELESS COMPRESSION DEVICE

(75) Inventor: Mark A. Vess, Hanson, MA (US)

(73) Assignee: Covidien LP, Mansfield, MA (US)

( * ) Notice: Subject to any disclaimer, the term of this patent is extended or adjusted under 35 U.S.C. 154(b) by 1059 days.

(21) Appl. No.: 12/241,936

(22) Filed: Sep. 30, 2008

(65) Prior Publication Data

US 2010/0081977 A1    Apr. 1, 2010

(51) Int. Cl.
*A61F 13/00*    (2006.01)
*A61H 9/00*    (2006.01)

(52) U.S. Cl.
USPC ............................................. 602/13; 601/152

(58) Field of Classification Search
USPC ............. 602/16, 26–29, 60–64, 13; 601/151, 601/152
See application file for complete search history.

(56) References Cited

U.S. PATENT DOCUMENTS

| | | |
|---|---|---|
| 1,928,992 A | 10/1933 | Clark et al. |
| 3,288,132 A | 11/1966 | Meredith |
| 3,699,945 A | 10/1972 | Hanafin |
| 3,826,249 A | 7/1974 | Lee et al. |
| 4,091,804 A | 5/1978 | Hasty |
| 4,372,297 A | 2/1983 | Perlin |
| D269,905 S | 7/1983 | Tamm |
| 4,402,312 A | 9/1983 | Villari et al. |
| 4,524,458 A | 6/1985 | Pongrass et al. |
| 4,579,555 A | 4/1986 | Russo |
| 4,702,235 A | 10/1987 | Hong |
| 4,804,208 A | 2/1989 | Dye |
| 5,135,469 A | 8/1992 | Castillo |
| 5,152,302 A | 10/1992 | Fareed |
| 5,310,400 A | 5/1994 | Rogers et al. |
| 5,312,431 A | 5/1994 | McEwen |
| 5,342,285 A | 8/1994 | Dye |
| 5,403,265 A | 4/1995 | Berguer et al. |
| 5,437,615 A | 8/1995 | Pekar et al. |
| 5,478,119 A | 12/1995 | Dye |
| 5,546,955 A | 8/1996 | Wilk |
| 5,578,055 A | 11/1996 | McEwen |
| 5,626,556 A | 5/1997 | Tobler et al. |
| 5,641,322 A | 6/1997 | Silver et al. |

(Continued)

FOREIGN PATENT DOCUMENTS

| | | |
|---|---|---|
| JP | 2006 333983 A | 12/2006 |
| JP | 58147520 U | 4/2012 |

(Continued)

OTHER PUBLICATIONS

European Search Report regarding related application serial No. EP 09170464.3 dated Feb. 1, 2010, 6 pgs.

(Continued)

*Primary Examiner* — Kim M Lewis
(74) *Attorney, Agent, or Firm* — John Paul Mello, Esq.

(57) ABSTRACT

A compression device for applying compression to a body part of a wearer has an inflatable bladder defined by first and second bladder layers and a bladder sealing line securing the first and second bladder layers to one another. A conduit is defined by spaced apart, generally opposing conduit sealing lines securing the first and second bladder layers to one another and portions of the first and second bladder layers between the conduit lines. The conduit is fluidly connected to the inflatable bladder for delivering pressurized air to the inflatable bladder. Tubing is not needed for connection to the compression device.

18 Claims, 7 Drawing Sheets

(56) References Cited

U.S. PATENT DOCUMENTS

| | | | |
|---|---|---|---|
| 5,725,485 A | 3/1998 | Ribando et al. | |
| 5,795,312 A | 8/1998 | Dye | |
| 5,827,243 A | 10/1998 | Palestrant | |
| 5,891,065 A | 4/1999 | Cariapa et al. | |
| 6,080,120 A | 6/2000 | Sandman et al. | |
| 6,102,252 A | 8/2000 | Overman et al. | |
| 6,155,263 A | 12/2000 | Weaver | |
| 6,203,510 B1 | 3/2001 | Takeuchi et al. | |
| 6,290,662 B1 | 9/2001 | Morris et al. | |
| 6,375,633 B1 | 4/2002 | Endress et al. | |
| 6,428,492 B2 | 8/2002 | Lloyd | |
| 6,554,785 B1 | 4/2003 | Sroufe et al. | |
| 6,579,252 B2 | 6/2003 | Lloyd et al. | |
| 6,585,669 B2 | 7/2003 | Manor et al. | |
| 6,589,194 B1 | 7/2003 | Calderon et al. | |
| 6,676,614 B1 | 1/2004 | Hansen et al. | |
| 6,685,661 B2 | 2/2004 | Peled | |
| 6,966,884 B2 | 11/2005 | Waldridge et al. | |
| 7,063,676 B2 | 6/2006 | Barak et al. | |
| 7,120,955 B2 | 10/2006 | Wang | |
| 7,127,762 B1 | 10/2006 | Lau | |
| 7,186,245 B1 | 3/2007 | Cheng et al. | |
| 7,270,642 B2 | 9/2007 | Ouchene et al. | |
| 7,284,291 B2 | 10/2007 | Wang | |
| 7,316,658 B2 | 1/2008 | Gagne | |
| 7,354,411 B2 | 4/2008 | Perry et al. | |
| 7,376,994 B2 | 5/2008 | Wu | |
| 7,384,425 B2 | 6/2008 | McEwen | |
| 7,442,175 B2 | 10/2008 | Meyer et al. | |
| 2002/0022791 A1 | 2/2002 | Morris et al. | |
| 2002/0115949 A1 | 8/2002 | Kuslich et al. | |
| 2003/0078674 A1 | 4/2003 | Phillips | |
| 2003/0181990 A1 | 9/2003 | Phillips | |
| 2004/0199090 A1 | 10/2004 | Sanders et al. | |
| 2005/0184264 A1 | 8/2005 | Tesluk et al. | |
| 2005/0187503 A1 | 8/2005 | Tordella et al. | |
| 2006/0258964 A1 | 11/2006 | Biondo et al. | |
| 2006/0287621 A1 | 12/2006 | Atkinson et al. | |
| 2007/0038167 A1 | 2/2007 | Tabron et al. | |
| 2007/0049852 A1 | 3/2007 | Linnane et al. | |
| 2007/0049853 A1 | 3/2007 | Adams et al. | |
| 2007/0055188 A1* | 3/2007 | Avni et al. | 601/151 |
| 2007/0088239 A1 | 4/2007 | Roth et al. | |
| 2007/0135743 A1 | 6/2007 | Meyer | |
| 2007/0249976 A1 | 10/2007 | Tucker et al. | |
| 2007/0249977 A1 | 10/2007 | Bonnefin et al. | |
| 2008/0015630 A1* | 1/2008 | Rousso | 606/202 |
| 2008/0177159 A1 | 7/2008 | Gavriely | |
| 2010/0081974 A1 | 4/2010 | Vess | |

FOREIGN PATENT DOCUMENTS

| | | |
|---|---|---|
| WO | 2007085828 A1 | 8/2007 |
| WO | 2008055304 A1 | 5/2008 |
| WO | 2008084225 A1 | 7/2008 |

OTHER PUBLICATIONS

European Search Report regarding related application serial No. EP 09172060 dated Feb. 2, 2010 6 pgs.

Japanese Application No. 2009-225612, Japanese Patent Office, Notification of Reason(s) for Refusal dated Feb. 14, 2012 with English translation, 10 pages, Japan.

Japanese Application No. 2009-225612, Japanese Patent Office, Decision of Refusal dated Aug. 1, 2012 with English translation, 7 pages, Japan.

U.S. Appl. No. 12/241,670, Non-Final Office action dated Aug. 15, 2012, 20 pages, Alexandria, Virginia, United States.

Japanese Application No. 2009-225612, Japanese Patent Office, Interrogatory dated Feb. 5, 2013 with English translation, 7 pages, Japan.

* cited by examiner

TUBELESS COMPRESSION DEVICE

FIELD OF THE INVENTION

The present invention generally relates to a compression device, particularly of the type used to prevent or treat medical conditions such as deep vein thrombosis.

BACKGROUND OF THE INVENTION

A major concern for immobile patients and like persons are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popiteal and tibial return, deoxygenated blood to the heart. For example, when blood circulation in these veins is retarded due to illness, injury or inactivity, there is a tendency for blood to accumulate or pool. A static pool of blood may lead to the formation of a blood clot. A major risk associated with this condition is interference with cardiovascular circulation. Most seriously, a fragment of the blood clot can break loose and migrate. A pulmonary emboli can form from the fragment potentially blocking a main pulmonary artery, which may be life threatening. The current invention can also be applied to the treatment of other conditions, such as lymphedema.

The conditions and resulting risks associated with patient immobility may be controlled or alleviated by applying intermittent pressure to a patient's limb, such as, for example, a leg to assist in blood circulation. For example, sequential compression devices have been used, such as the device disclosed in U.S. Pat. No. 4,091,804 to Hasty. Sequential compression devices are typically constructed of two sheets of material secured together at the seams to define one or more fluid impervious bladders, which are connected to a source of pressure for applying sequential pressure around a patient's body parts for improving blood return to the heart. The inflatable sections are covered with a laminate to improve durability, patient comfort, and to protect against puncture. As part of the compression device, the two sheets are structurally designed to withstand a changing pressure over time under repeated use. Medical tubing is used to make connection of the source of pressure to the usually several bladders of the compression device. The source of air pressure is an air compressor most often located remotely from the patient.

SUMMARY OF THE INVENTION

In one aspect of the present invention, a compression device for applying compression to a body part of a wearer generally comprises a first bladder layer integrally formed as a one-piece sheet of air impermeable material, and a second bladder layer integrally formed as a one-piece sheet of air impermeable material. The first and second bladder layers are disposed in opposing relationship to one another. An inflatable bladder is defined by the first and second bladder layers and a bladder sealing line securing the first and second bladder layers to one another. A plurality of conduits are each defined by spaced apart, generally opposing conduit sealing lines securing the first and second bladder layers to one another and portions of the first and second bladder layers between the conduit lines. At least one of the conduits is fluidly connected to the inflatable bladder for delivering pressurized air to the inflatable bladder. A conduit terminal supported by the compression device has passages therein. For each conduit at least one of the first and second bladder layers are sealingly joined to the conduit terminal at a respective one of the passages to form a fluid-tight connection between the conduit terminal and the conduit whereby the passage and conduit are in fluid communication.

In another aspect of the present invention, a compression device for applying compression to a body part of a wearer generally comprises a first bladder layer integrally formed as a one-piece sheet of air impermeable material and a second bladder layer integrally formed as a one-piece sheet of air impermeable material. The first and second bladder layers are disposed in opposing relationship to one another. An inflatable bladder is defined by the first and second bladder layers and a bladder sealing line securing the first and second bladder layers to one another. At least one conduit is defined by spaced apart, generally opposing conduit sealing lines securing the first and second bladder layers to one another and portions of the first and second bladder layers between the conduit sealing lines. The conduit is fluidly connected to the inflatable bladder for delivering pressurized air to the inflatable bladder. A conduit terminal supported by the compression device has a passage therein. At least one of the first and second bladder layers is sealingly joined to the conduit terminal at a respective one of the passages to form a fluid-tight connection between the conduit terminal and the conduit whereby the passage and conduit are in fluid communication. The conduit terminal comprises a snap connector component for snap connection to the air compressor unit. The snap connector component includes a fluid passage therein in fluid communication with the conduit and adapted for fluid communication with the air compressor unit upon connection thereto.

In yet another aspect of the present invention, a method of making a compression device generally comprises sealing opposing first and second bladder layers to one another along a bladder sealing line to define an inflatable chamber. Each of the first and second bladder layers is integrally formed as a one-piece sheet of air impermeable material. The first and second bladder layers are sealed to one another along opposing conduit sealing lines to define an elongate conduit in fluid communication with the inflatable chamber for delivering pressurized air to the inflatable chamber. A conduit terminal is provided that includes a passage therein. At least one of the first and second bladder layers is joined to the conduit terminal to establish fluid communication between the passage and the conduit.

Other objects and features will be in part apparent and in part pointed out hereinafter.

DETAILED DESCRIPTION OF THE DRAWINGS

Figure 1:
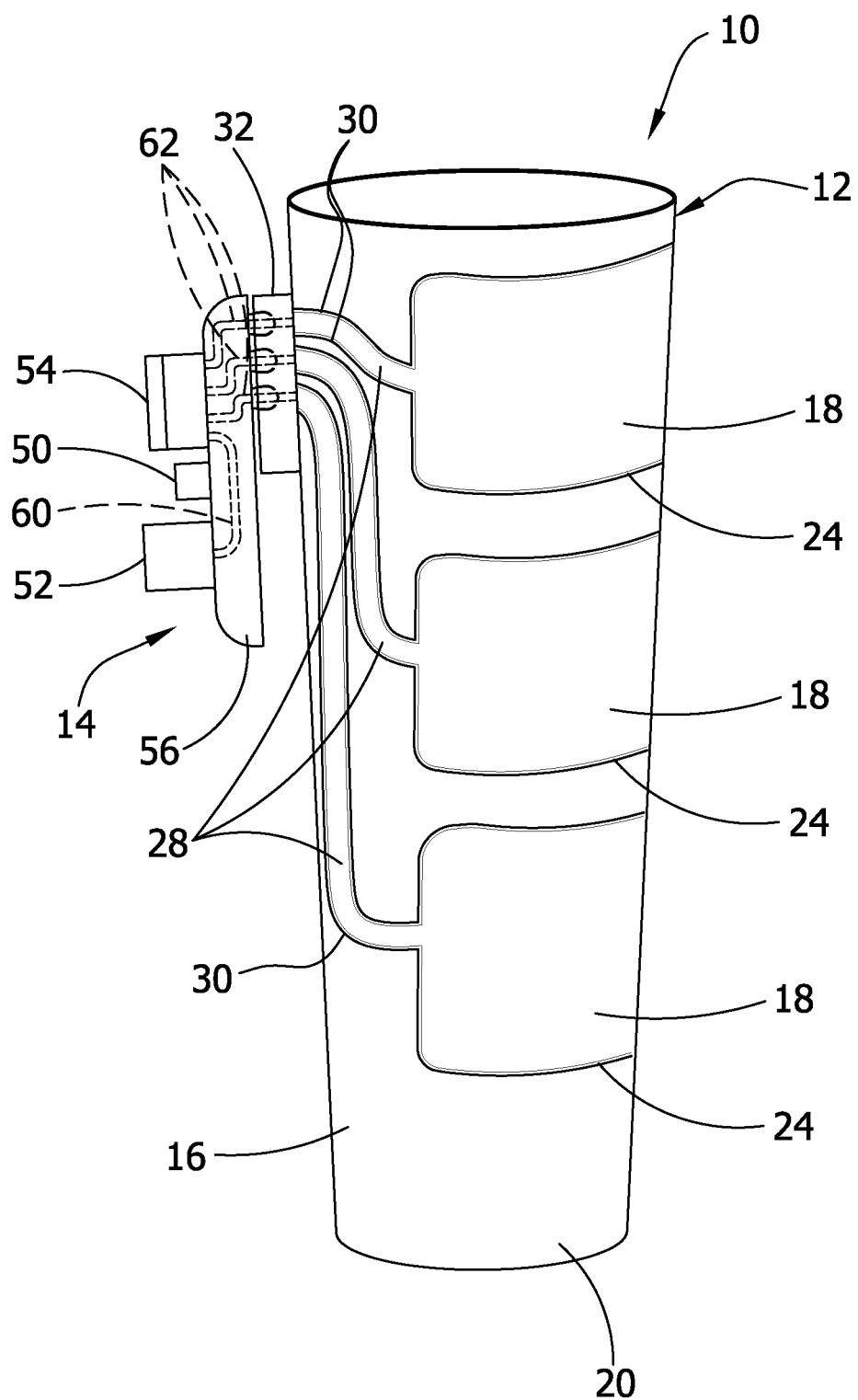
FIG. 1 is a perspective of a compression device assembly in a closed, wrapped configuration.

Referring now to the drawings and in particular to FIG. 1, a compression device assembly for applying compression therapy to a body part of a wearer is generally indicated 10. The compression device assembly includes a compression device, generally indicated at 12, and a portable controller unit, generally indicated at 14, mounted on the compression device.

Figure 2:
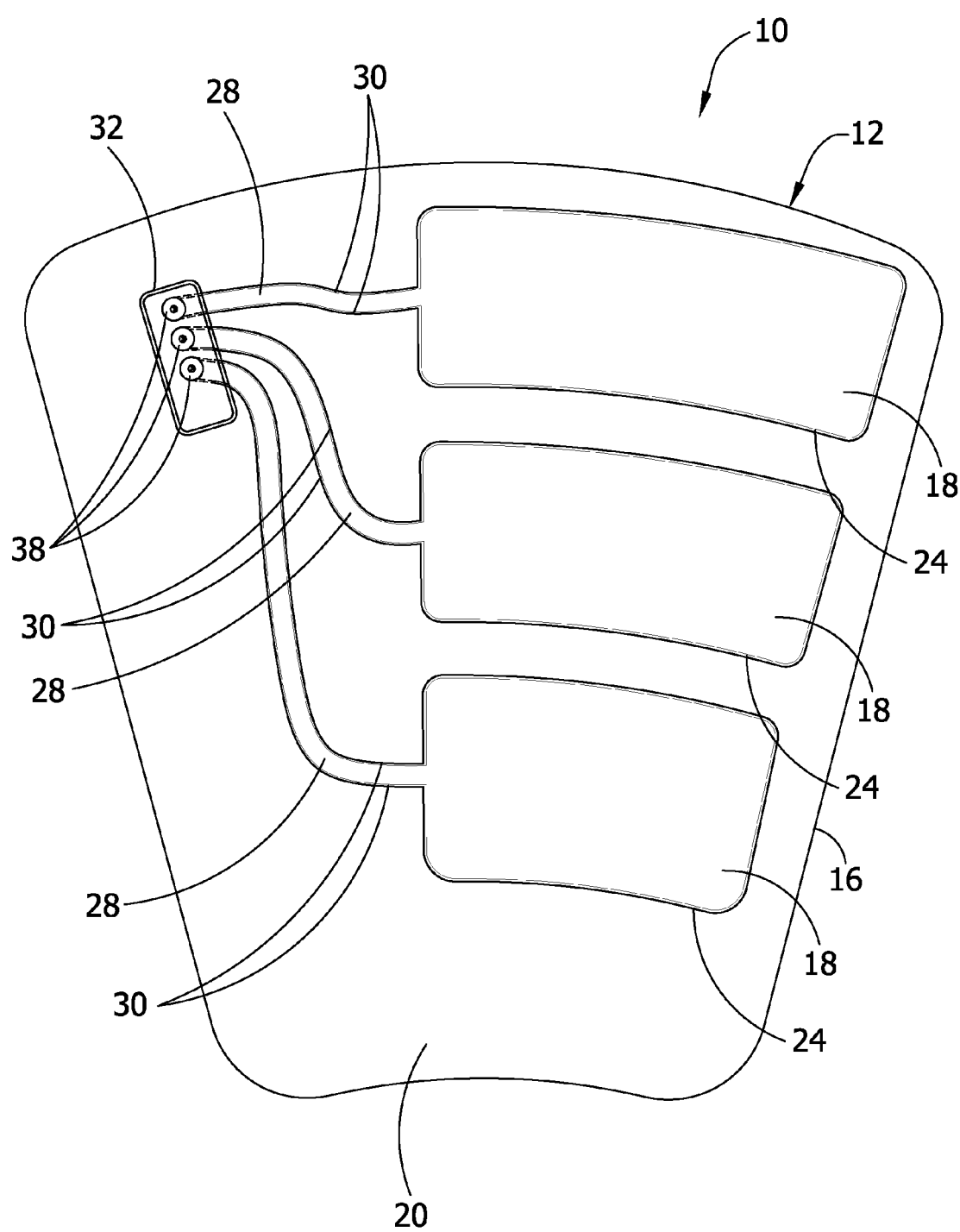
FIG. 2 is a plan view of a compression device of the compression device assembly in an open, unwrapped configuration.
Figure 3:
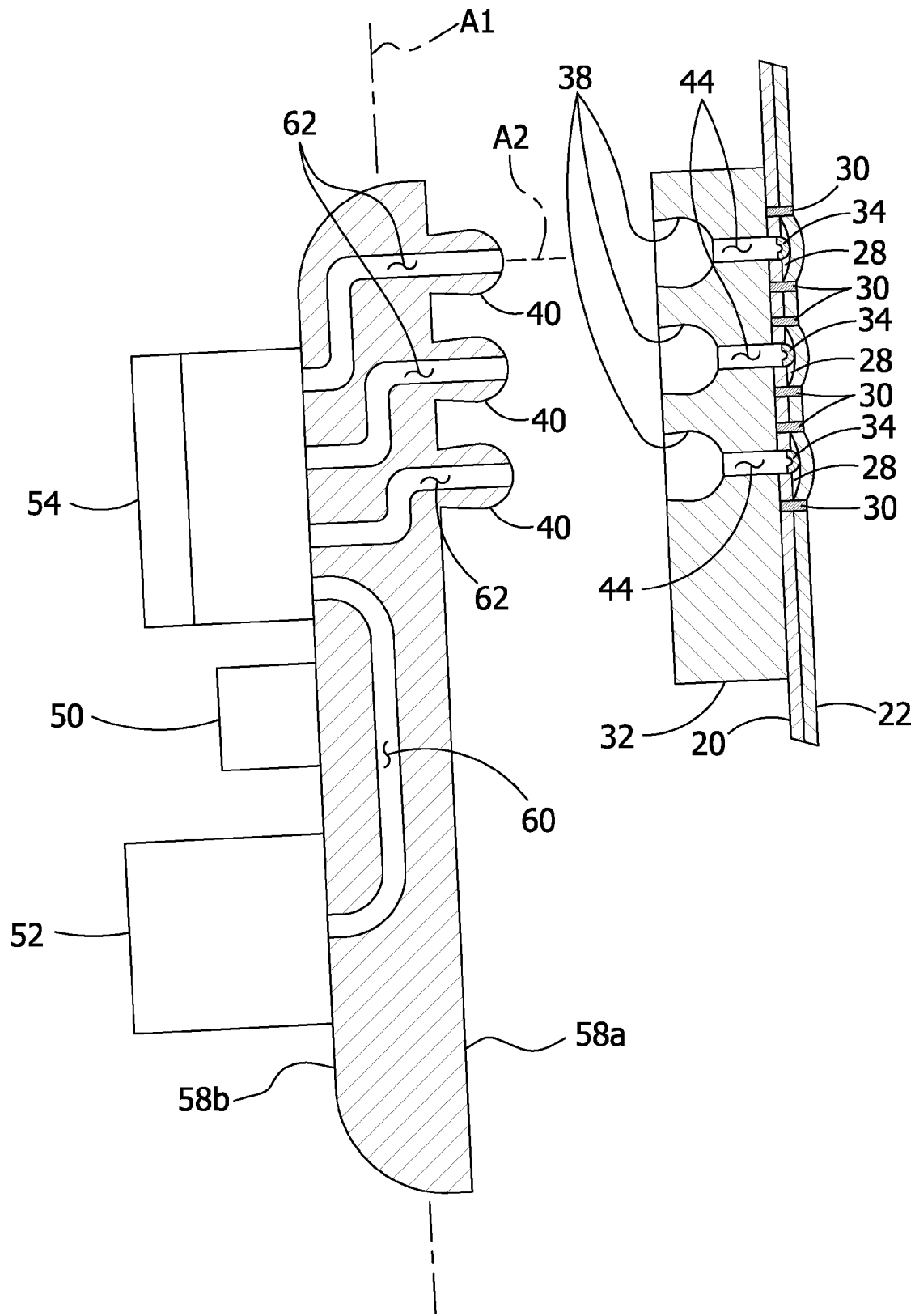
FIG. 3 is an enlarged, fragmentary section of the compression device assembly showing a portable controller unit exploded from a mount.

Referring to FIGS. 1-3, the compression device 12 of the illustrated embodiment is sized and shaped to be wrapped around a leg of a wearer. The compression device 12 includes an inflatable member 16 having three spaced apart inflatable bladders 18. The number and/or configuration of bladders may be other than shown in the illustrated embodiment. The inflatable member 16 comprises opposing inner and outer bladder layers 20, 22, respectively, secured to one another along upper, intermediate and lower bladder sealing lines 24. As used herein, the terms "inner" and "outer" refer to relative positions with respect to the wearer's leg when the device 12 is wrapped around the leg. The sealing lines 24 together with portions of the bladder layers 20, 22 within the perimeters of the lines define respective inflatable bladders 18 that are capable of retaining pressurized air. In one embodiment, each bladder layer 20, 22 is integrally formed as a single sheet of material. For example, each bladder layer 20, 22 may be formed from a single sheet of air impermeable material, such as PVC, or may be a laminated material. Further, the bladder layers 20, 22 may be welded to one another along the bladder sealing lines 24, although other ways of forming the bladder lines and the inflatable bladders are within the scope of the invention. Although not illustrated, the compression device 12 may include an inner layer or liner for contacting the skin of the wearer and an outer layer forming the exterior surface of the device. Other configurations are within the scope of the present invention.

Referring to FIGS. 1-6, conduits 28 in fluid communication with the respective inflatable bladders 18 extend from the inflatable bladders to a mount 32 (broadly, "a conduit terminal") on which the portable controller unit 14 (or "air compressor unit") is mounted, as will explained in detail below. The conduits 28 are used to deliver pressurized air from the controller unit 14 to the inflatable bladders 18 during use. Each conduit 28 is formed by a pair of spaced apart, generally opposing conduit sealing lines 30 that secure the bladder layers 20, 22 to one another. Each pair of conduit lines 30 and portions of the bladder layers 20, 22 between the pair of lines define one of the conduits 28. As with the bladder sealing lines 24, the bladder layers 20, 22 may be welded to one another along the conduit sealing lines 30. Further, as in the illustrated embodiment, each bladder 18 and associated conduit 28 may be formed by a single, continuous line. For example and without being limiting, a single welding operation may form a continuous sealing line that includes the bladder sealing line 24 and the pair of conduit sealing lines 30 of one of the bladders 18 and its associated conduit 28.

Referring to FIGS. 3-6, a spacer 34 is received in each conduit 28 for maintaining the conduit open along its length so that the conduit remains in fluid communication with the controller unit 14 during use. Each spacer 34 is generally elongate and generally flexible along its length so that the spacer is able to conform to the path of the conduit 28. As shown best in FIG. 5, each spacer 34 has a generally U-shaped cross section and a height extending between the opposing bladder layers 20, 22 in the conduit. Each spacer 34 is substantially incompressible along its height, or at least will not completely collapse under normal conditions. Through this configuration, the conduits 28 remain open and the bladders 18 remain in fluid communication with the controller unit 14 despite any compressive forces being applied to the device 12 (e.g., the weight of the wearer's leg) that may close or otherwise impede fluid flow between the controller unit and one or more of the inflatable bladders. In one example, each spacer 34 is constructed of PVC or silicone, including extrudable silicone, and may be formed by extrusion or from stock.

Referring to FIGS. 1-3A, the mount 32 on which the portable controller unit 14 is mounted is secured to an exterior surface of the outer bladder layer 20. The mount 32 includes internal female connector components 38 for receiving mateable male connector components 40 of the portable controller unit 14 to releasably mount the controller unit on the compression device 12. It is understood that the mount 32 may include male connection components for being received in mateable female connector components of the portable controller unit 14 within the scope of the invention. In the illustrated embodiment, the male connection components 40 are releasably retained in the female connection components 38 by snap-fit engagement. The male connector components 40 have a slightly bulbous shape and the female connector components 38 ("receptacles") have a corresponding shape. The widest part of the male connector component 40 is wider than a mouth of the female connector component 38 so that the male component and/or female component are deformed as the male component enters the female connector component. Once the male connector component 40 is inserted far enough into the female connector component 38, it reaches a wider portion of the female connector component and "snaps" back toward its original shape. It will be appreciated that the connector components 38, 40 thereafter resist separation. However, upon application of sufficient force, the connector components 38, 40 can be disconnected. Other ways of releasably mounting the portable controller unit 14 on the compression device 12, including mateable snap-fit components, are within the scope of the invention.

Figure 3A:
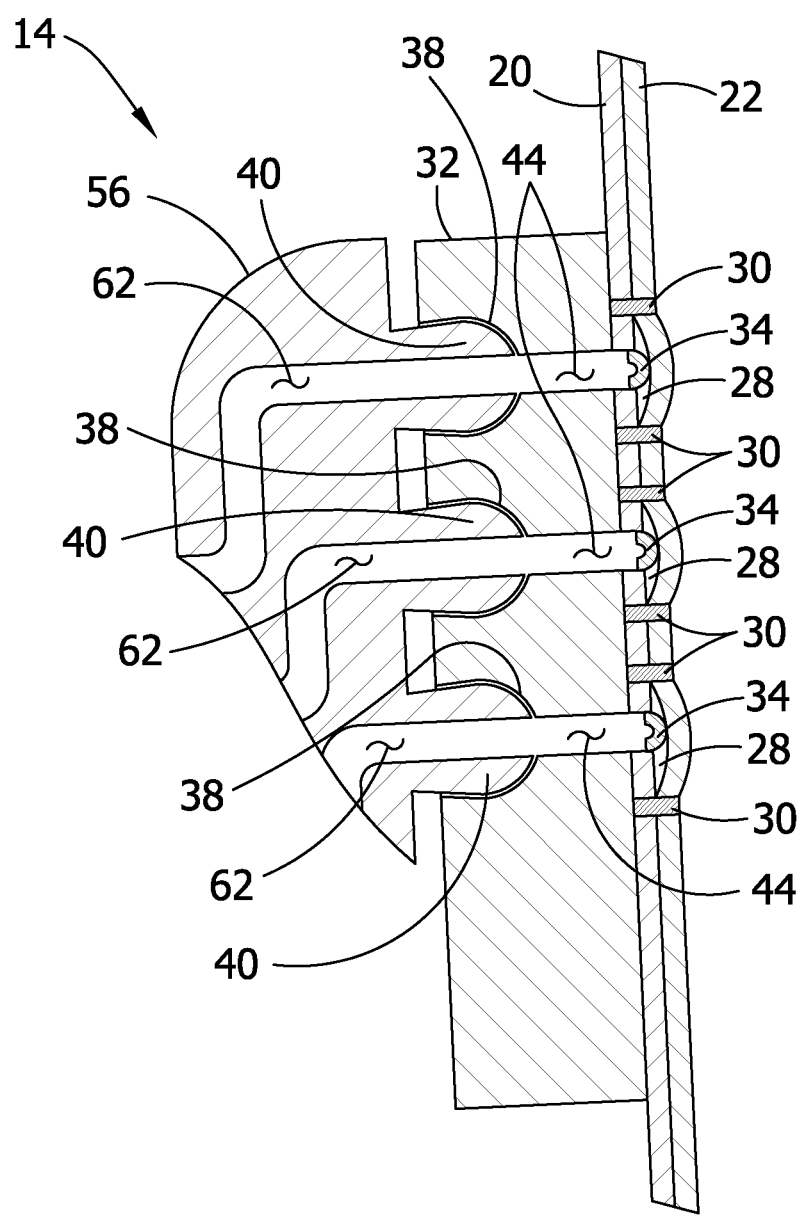
FIG. 3A is an enlarged, fragmentary view of FIG. 3 with the portable controller unit connected to the mount.
Figure 4:
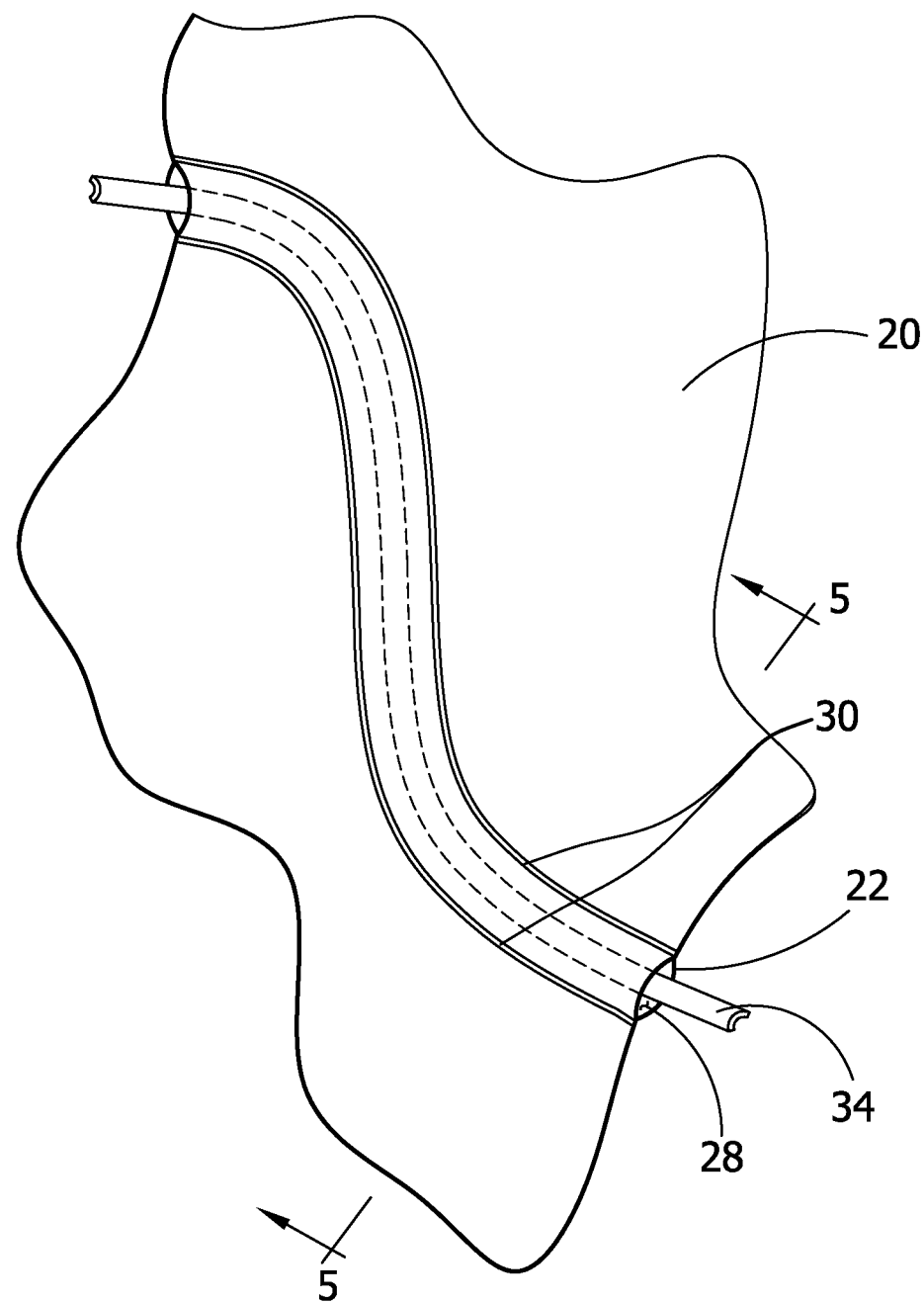
FIG. 4 is an enlarged, fragmentary view of a portion of the compression device.
Figure 5:
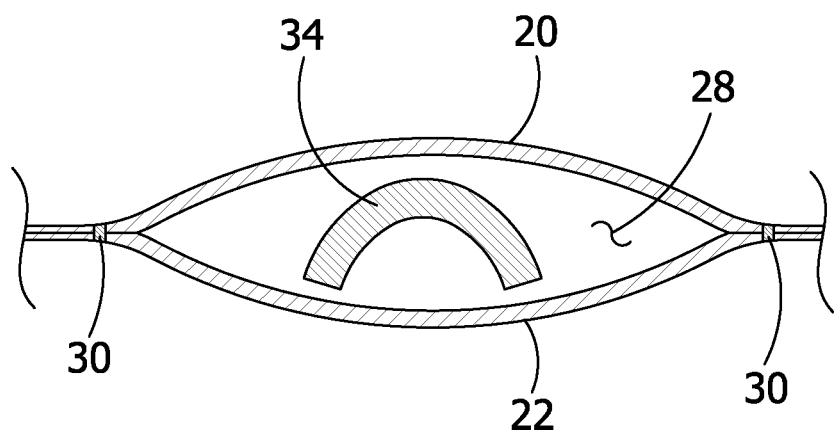
FIG. 5 is an enlarged section of the compression device taken along the line 5-5 in FIG. 4.
Figure 6:
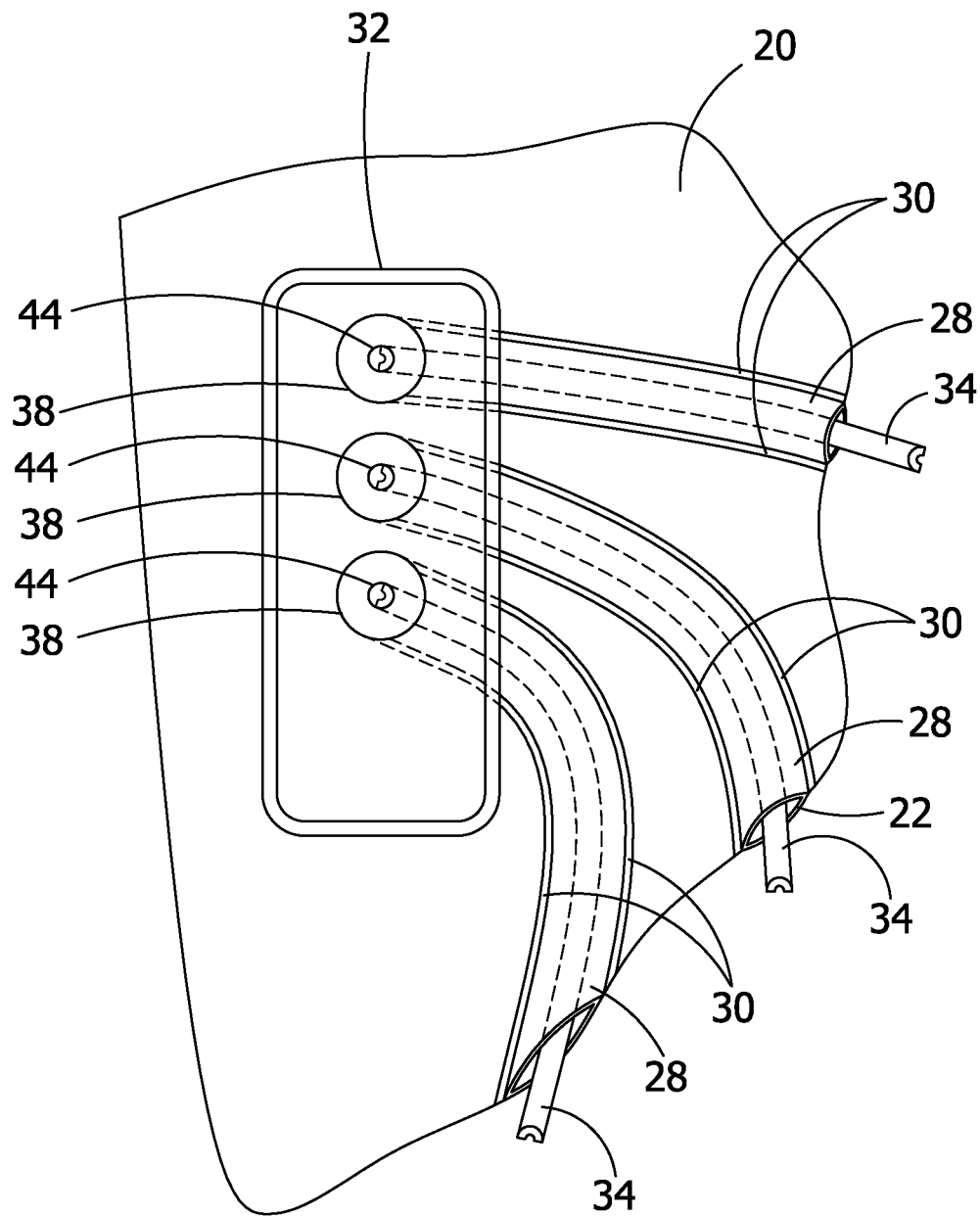
FIG. 6 is an enlarged, fragmentary view of the compression device.

Referring to FIGS. 3 and 3A, each female connector component 38 of the mount 32 is fluidly connected to one of the conduits 28 via an inlet passage 44 inside the mount. In one example, the mount 32, including the female connector components 38 and the inlet passages 44, is molded as a one-piece unit. Other ways of forming the mount 32 are within the scope of the invention. The mount 32 is secured to the inner and outer bladder layers 20, 22 by heat welding (e.g., radiofrequency (RF) welding), adhesive, mechanical connectors or in other ways so that the inlet passages 44 in the mount are in sealed, fluid communication with the respective bladder conduits 28. For example and without being limiting, in one method the mount 32 is placed in an RF welding die together with a sheet that will become the inner bladder layer 20, and the sheet is welded to the mount 32 around the inlet passage 44. The outer bladder layer 22 and spacers 34 (one for each conduit 28 to be formed) are next placed in the welding die. A second weld is formed connecting the inner and outer bladder layers 20, 22 together and connecting both layers to the mount 32 from each inlet passage 44 to the periphery of the mount, thereby forming a small section of the conduit 28. A U-shaped die member (not shown) is used for this procedure so that the small section of the conduit 28 is left open at the periphery of the mount 32. A third welding step joins the inner and outer bladder layers 20, 22 together to form the remainder of each conduit 28, as well as the bladders 18. The spacers 34 are encapsulated in the conduits 28 in the third welding step. Two different welding steps are used to form the conduits 28 because of the difference in thickness of material when the mount 32 is present in the weld line, versus when the mount is not part of the weld. However it is envisioned that the conduits 28 could be formed in a single step with a properly tuned weld die.

Referring to FIG. 1, the portable controller unit 14 includes a controller 50 electrically connected to an air compressor 52 and a valve mechanism 54. Each of the components 50, 52, 54 is mounted on a manifold base 56 (broadly, a base). As explained below, the male connection components 40 extend outward from the manifold base 56. More specifically, the male connection components 40 extend outward from a first face 58a (FIG. 3) of the base 56 and the controller 50, air compressor 52 and valve mechanism 54 are mounted on an opposite second face 58b (FIG. 3) of the base. In the illustrated embodiment, a longitudinal axis A1 of the base 56 is generally orthogonal to axes A2 (only one is illustrated) of the connection components 40. The controller 50 may be a microprocessor that communicates with the air compressor 52 and the valve mechanism 54 during operation. The valve mechanism 54 may comprise a plurality of valves (e.g., solenoid valves) that are controlled by the microprocessor. Although not illustrated in the drawings, the controller unit may include a rechargeable, portable power source, such as a battery for supplying power to the controller 50, the air compressor, 52 and the valve mechanism 54. The operation of the portable controller unit 14 may operate generally in the same manner as taught in the art.

Referring to FIGS. 1 and 3, the manifold base 56 includes a single internal inlet plenum 60 and a plurality of internal outlet plenums 62 extending through the male connector components 40. The inlet plenum 60 fluidly connects the air compressor 52 and the valve mechanism 54. The inlet plenum 60 extends from the second face 58b of the manifold base 56 at a first location to a second location on the second face. The air compressor 52 is mounted on the second face 58b of the base 56 in fluid communication with the inlet plenum 60 at the first location. The outlet plenums 62 fluidly connect the valve mechanism 54 and the male connector components 40. The outlet plenums 62 extend through the second face 58b of the base 56 at third location and extend axially through the male connector components 40 to fluidly connect the valve mechanism 54 to the respective conduits 28 and the respective bladders 18. The valve mechanism 54 is mounted on the second face 58b of the base 56 in fluid communication with both the inlet plenum 62 at the second location and the outlet plenums 62 at the third locations. In one example, the manifold base 56, including the inlet plenum 60, the outlet plenums 62 and the male connector components 40, is molded as a single, integral unit. For example, the base 56 and the male components 40 may be formed from a resilient polymeric material. It is understood that the base 56 may be formed in other ways without departing from the scope of the present invention. The portable controller unit 14 may also include a cover (not shown) detachably secured to the manifold base 56 to enclose the controller 50, the air compressor 52 and the valve mechanism 54.

In an exemplary use, the compression device assembly 10 is wrapped around a limb, e.g., a leg, of a patient. Mateable fasteners, such as hook and loop fasteners (not shown), that are adjacent to opposite lateral edges of the compression device 12 may be used to releasably secure the compression device to the wearer's limb, as is generally known in the art. Before or after the compression device 12 is secured to the wearer's limb, the portable controller unit 14 is mounted on the device by inserting the male connection components 40 into the respective female connection components 38 in the mount 32. As explained above, the male connection components 40 are retained in the female connection components 38 by snap-fit engagement. With the controller unit 14 mounted on the device 12, the controller unit is in fluid communication with the inflatable bladders 18. The controller 50 can be activated to begin compression therapy, whereby the air compressor 52 delivers pressurized air via the inlet plenum 60 in the manifold base 56 to the valve mechanism 54, which diverts the air into one of the three outlet plenums 62 and into the appropriate bladder 18 via one of the conduits 28. The portable controller unit 14 can be detached from the compression 12 by simply pulling the base 56 away from the mount 32 so that the male connection components 40 disengage the female connection components 38 in the mount 32. It will be appreciated that separate tubing for delivering air is eliminated in the illustrated embodiment. It is envisioned that the compression device 12 may be disposable and constructed for one-time use. Thus, the portable controller unit 14 having a rechargeable power source can be reused and mounted on another compression device 12 of the same type.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A compression device for applying compression to a body part of a wearer, the compression device comprising:
    a first bladder layer integrally formed as a one-piece sheet of air impermeable material;
    a second bladder layer integrally formed as a one-piece sheet of air impermeable material, the first and second bladder layers being disposed in opposing relationship to one another;
    an inflatable bladder defined by the first and second bladder layers and a bladder sealing line securing the first and second bladder layers to one another;
    a plurality of conduits, each conduit being defined by spaced apart, generally opposing conduit sealing lines securing the first and second bladder layers to one another and portions of the first and second bladder layers between the conduit sealing lines, at least one of the conduits being fluidly connected to the inflatable bladder for delivering pressurized air to the inflatable bladder;
    a unitary conduit terminal supported by the compression device and having passages therein, for each conduit at least one of the first and second bladder layers being sealingly joined to the conduit terminal at a respective one of the passages to form a fluid-tight connection between the conduit terminal and the conduit whereby the passage and conduit are in fluid communication;
    a portable air compressor unit mounted on the compression device and to fluidly connect the air compressor unit to the conduits to deliver pressurized air from the air compressor unit to the inflatable bladder without tubing fluidly connecting the portable air compressor unit to the compression device.

2. A compression device as set forth in claim 1 wherein the second bladder layer is sealingly attached to the conduit terminal.

3. A compression device as set forth in claim 1 wherein the conduit terminal is adapted for snap-together connection with the air compressor unit to mount the air compressor unit on the conduit terminal.

4. A compression device as set forth in claim 3 wherein the conduit terminal comprises a snap connector component for snap connection to the air compressor unit, the snap connector component including a fluid passage therein in fluid communication with the conduit and adapted for fluid communication with the air compressor unit upon connection thereto.

5. A compression device as set forth in claim 4 wherein the snap connector component comprises a receptacle.

6. A compression device as set forth in claim 1 wherein the inflatable bladder comprises a plurality of inflatable bladders formed by the first and second layers and by bladder sealing lines each of the conduits being in fluid communication with respective ones of the inflatable bladders.

7. A compression device as set forth in claim 1 in combination with the air compressor unit.

8. A compression device as set forth in claim 1 wherein the conduit terminal is molded as one piece of material.

9. A compression device as set forth in claim 1 further comprising spacing members within the conduits for spacing apart the portions of the first and second bladder layers between the conduit lines, whereby the conduits remain open during use.

10. A compression device as set forth in claim 9 wherein the spacing members each comprise an elongate body having a generally U-shaped cross section.

11. A method of making a compression device comprising:
sealing opposing first and second bladder layers to one another along a bladder sealing line to define at least one inflatable chamber, each of the first and second bladder layers being integrally formed as a one-piece sheet of air impermeable material;
sealing the first and second bladder layers to one another along opposing conduit sealing lines to define elongate conduits, at least one of which is in fluid communication with the inflatable chamber for delivering pressurized air to the inflatable chamber;
providing a unitary conduit terminal including passages therein and a portable air compressor unit on the compression device to fluidly connect the air compressor unit to the conduits to deliver pressurized air from the air compressor unit to the inflatable bladder without tubing fluidly connecting the portable air compressor unit to the compression device;
joining at least one of the first and second bladder layers to the conduit terminal to establish fluid communication between each of the passages and a respective one of the conduits.

12. A method as set forth in claim 11 wherein said sealing opposing first and second bladder layers to define the inflatable chamber and said sealing the first and second bladder layers to define the elongate conduit are performed substantially simultaneously.

13. A method as set forth in claim 11 wherein said sealing opposing first and second bladder layers to define the inflatable chamber and said sealing the first and second bladder layers to define the elongate conduit are performed by radiofrequency welding.

14. A method as set forth in claim 11 further comprising releasably securing a portable controller unit to the conduit terminal of the compression device in fluid communication with the conduit and the inflatable chamber.

15. A method as set forth in claim 14 wherein releasably securing the portable controller comprises snap-connecting the portable controller to the conduit terminal.

16. A method as set forth in claim 11 wherein joining at least one of the first and second bladder layers to the conduit terminal comprises joining the first bladder layer to the conduit terminal.

17. A method as set forth in claim 16 wherein sealing the first and second bladder layers together to form a conduit comprises, following joining the first bladder layer to the conduit terminal, the step of joining the first and second bladder layers to each other and to the conduit terminal.

18. A method as set forth in claim 11 further comprising providing a spacing member within the conduit for spacing apart the portions of the first and second bladder layers between the conduit sealing lines, whereby the conduit remains open during use.

* * * * *